United States Patent
West et al.

(10) Patent No.: US 9,931,098 B2
(45) Date of Patent: Apr. 3, 2018

(54) POST ACQUISITION CALIBRATION

(71) Applicant: Carestream Health, Inc., Rochester, NY (US)

(72) Inventors: Frank West, Marion, NY (US); Nathan J. Packard, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 15/098,610

(22) Filed: Apr. 14, 2016

(65) Prior Publication Data

US 2017/0296137 A1 Oct. 19, 2017

(51) Int. Cl.
| | |
|---|---|
| G06K 9/00 | (2006.01) |
| A61B 6/00 | (2006.01) |
| G06T 11/00 | (2006.01) |
| A61B 6/03 | (2006.01) |

(52) U.S. Cl.
CPC ............ A61B 6/583 (2013.01); A61B 6/032 (2013.01); A61B 6/4007 (2013.01); A61B 6/4085 (2013.01); G06T 11/008 (2013.01); G06T 2207/10081 (2013.01); G06T 2207/30168 (2013.01)

(58) Field of Classification Search
CPC .... A61B 6/583; G06T 11/006; Y10S 378/901
See application file for complete search history.

(56) References Cited

U.S. PATENT DOCUMENTS

| | | | |
|---|---|---|---|
| 5,214,578 A | 5/1993 | Cornuejols et al. | |
| 5,774,519 A | 6/1998 | Lindstrom et al. | |
| 6,275,559 B1* | 8/2001 | Ramani ................. | A61B 6/583 378/207 |
| 6,325,539 B1* | 12/2001 | Bromberg ............. | A61B 6/583 378/19 |
| 6,345,114 B1 | 2/2002 | Mackie et al. | |
| 6,466,638 B1 | 10/2002 | Silver et al. | |
| 6,715,918 B2 | 4/2004 | Mitschke et al. | |
| 6,851,855 B2 | 2/2005 | Mitschke et al. | |
| 7,016,456 B2 | 3/2006 | Basu et al. | |
| 7,186,023 B2 | 3/2007 | Morita et al. | |
| 7,269,243 B2 | 9/2007 | Chell et al. | |
| 7,559,694 B2 | 7/2009 | Gorges et al. | |
| 7,780,351 B2 | 8/2010 | Heigl et al. | |
| 7,945,022 B2 | 5/2011 | Nelms et al. | |
| 7,950,849 B2 | 5/2011 | Claus et al. | |
| 8,043,003 B2 | 10/2011 | Vogt et al. | |
| 2003/0161442 A1* | 8/2003 | Zeiss .................... | A61B 6/583 378/207 |

(Continued)

FOREIGN PATENT DOCUMENTS

CN 101750021 5/2011

*Primary Examiner* — Bhavesh Mehta
*Assistant Examiner* — Ian Lemieux

(57) ABSTRACT

A method of operating a tomographic imaging system whereby a plurality of radiographic images of an object are captured at a first orientation of the system's source and detector. After the radiographic images are captured and stored, geometric calibration data for the system is measured, corresponding to the first orientation of the system. A three dimensional image of the object is reconstructed using the measured geometric calibration data corresponding to the first orientation.

19 Claims, 4 Drawing Sheets

(56) References Cited

U.S. PATENT DOCUMENTS

| | | | |
|---|---|---|---|
| 2005/0201524 A1* | 9/2005 | Heumann | G01D 3/022 378/207 |
| 2008/0262345 A1* | 10/2008 | Fichtinger | A61B 6/504 600/426 |
| 2009/0296893 A1* | 12/2009 | Strobel | A61B 6/032 378/207 |
| 2011/0015519 A1* | 1/2011 | Graumann | A61B 6/583 600/424 |
| 2012/0076259 A1 | 3/2012 | Holt | |
| 2012/2021438 | 8/2012 | Vermandel et al. | |
| 2013/0010920 A1* | 1/2013 | Wein | G06T 11/008 378/19 |
| 2013/0230150 A1* | 9/2013 | Weiss | A61B 6/4233 378/207 |
| 2013/0266178 A1* | 10/2013 | Jain | G06T 7/70 382/103 |

\* cited by examiner

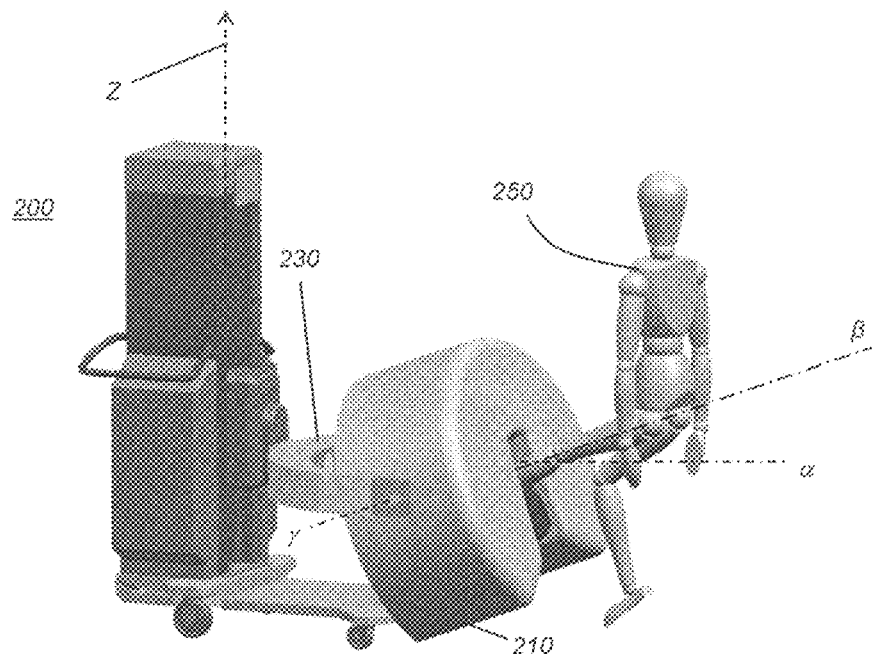
FIG. 2C
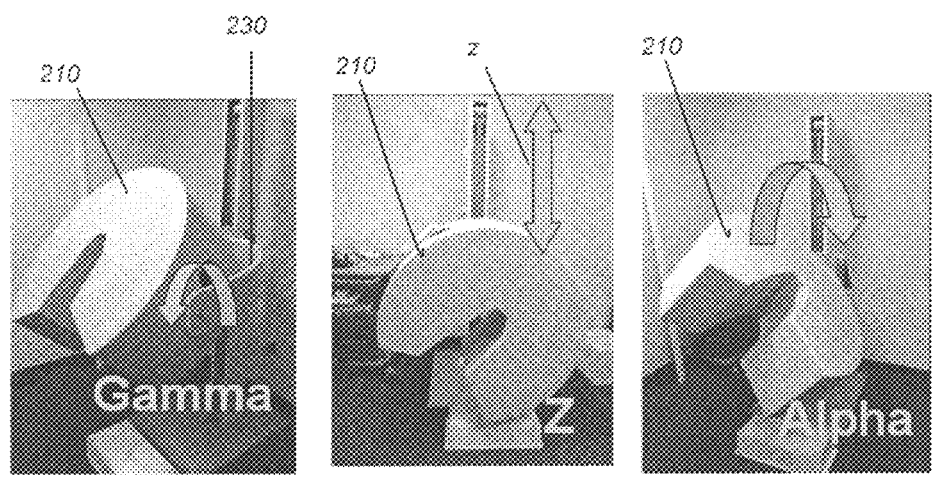
FIG. 3A  FIG. 3B  FIG. 3C

POST ACQUISITION CALIBRATION

CROSS REFERENCE TO RELATED APPLICATIONS

This application is related in certain respects to U.S. patent application Ser. No. 14/048,599, filed Oct. 8, 2013, in the name of Litzenberger et al., and entitled EXTREMITY IMAGING APPARATUS FOR CONE BEAM COMPUTED TOMOGRAPHY; and to U.S. patent application Ser. No. 14/879,136, filed Oct. 9, 2015, in the name of Simon, and entitled ITERATIVE RECONSTRUCTION PROCESS which are hereby incorporated by reference herein as if fully set forth in their entirety.

BACKGROUND OF THE INVENTION

The invention relates generally to diagnostic imaging using tomographic imaging systems such as cone beam imaging systems to obtain volume images of patient anatomies. Three dimensional radiographic imaging techniques may be used to generate accurate volume images of patient anatomies using reconstruction algorithms during tomosynthesis and tomography image processing, such as in cone beam computed tomography (CBCT) systems using one or more radiation sources. The subject matter disclosed herein relates to calibrating radiographic image reconstruction using geometric calibration.

3-D volume imaging has proved to be a valuable diagnostic tool that offers significant advantages over earlier 2-D radiographic imaging techniques for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

CBCT technology offers considerable promise as one type of diagnostic tool for providing 3-D volume images. CBCT systems capture volumetric data sets by using a high frame rate digital radiography (DR) detector and an x-ray source, which are typically affixed to a gantry that rotates about the object to be imaged and directs a divergent cone beam of x-rays toward the object from various points along its orbit around the object. The CBCT system captures projection images throughout the rotation, for example, one 2-D projection image at every degree of rotation. The projections are then reconstructed into a 3-D volume image using various reconstruction techniques. Among well known methods for reconstructing the 3-D volume image from the 2-D image data are filtered back projection approaches.

Although 3-D images of diagnostic quality can be generated using CBCT systems and technology, a number of technical challenges remain. In some cases, for example, the ability to correct poor image quality may be lacking as a result of not having geometric calibration data for a particular orientation of the gantry assembly used in the patient scan or exam. Geometric calibration for computed tomography (CT) and CBCT imaging systems provides an accurate representation of the imaging system's geometry during a scan which results in accurate 3-D volume reconstructions. Systems that operate under different loading conditions (vertical vs. horizontal, weight bearing, non-weight bearing, etc.) benefit from having available multiple geometric calibration data under each of these conditions. The present invention is directed to a method that allows obtaining geometric calibration data after a patient scan is completed by using similar conditions and parameters as in the patient scan. Typical CT and CBCT systems may be geometrically calibrated prior to performing patient scans, however, situations may occur wherein the imaging system components' position may be unanticipated prior to a patient scan, which may result in poor image quality due to less than optimal geometric calibration. In such a scenario—an additional geometrical calibration can be performed after the patient scan is completed, whose calibration data can then be used to produce a higher quality 3-D reconstruction.

Geometric calibration data may include specific cone-beam imaging geometry, such as the distance between the source and the digital detector, the dimensions of the detector, as well as the distribution of the photosensitive elements over the receiving surface of the digital detector. In another aspect, an x-ray beam path may be computationally modeled as being divided at equidistance points along its length equivalent to a voxel side length. The value of each dividing point may be an interpolation of the values of its nearest voxel neighbors. A 2-D image projection datum associated with an x-ray beam path may be modeled as the sum of incremental attenuation contributions from all the dividing points (voxels) along the beam's path. This model may be used to form a computational matrix useful for 3-D image reconstruction.

In summary, for tomographic imaging systems a number of improvements may be advantageous in systems having variable gantry or other equipment orientations including the following: (i) system flexibility for imaging at different heights with respect to the rotational axis of the source and detector, including the flexibility to allow imaging with the patient standing or seated comfortably, such as with a foot in an elevated position, for example; (ii) capability to adjust the angle of the rotational axis to suit patient positioning requirements; (iii) improved patient accessibility, so that the patient does not need to contort, twist, or unduly stress limbs or joints that may have been injured in order to provide images of those body parts; (v) improved ergonomics for obtaining the image, allowing the patient to stand or sit with normal posture, for example, and (vi) adaptability for multi-use imaging, allowing a single imaging apparatus to be configurable for imaging any of a number of extremities, including knee, ankle, toe, hand, elbow, and other extremities. The capability for straightforward configuration and positioning of the imaging apparatus allows the advantages of CBCT imaging to be adaptable for use with a range of extremities, to obtain volume images under a suitable imaging modality, with the image extremity presented at a suitable orientation under both load-bearing and non-load-bearing conditions, and with the patient appropriately standing or seated.

The discussion above is merely provided for general background information and is not intended to be used as an aid in determining the scope of the claimed subject matter.

BRIEF DESCRIPTION OF THE INVENTION

A method of operating a tomographic imaging system is disclosed. A number of radiographic images of an object are captured at a first orientation of the imaging system's source and detector. After the radiographic images are captured and stored, geometric calibration data for the system is generated (e.g., measured), corresponding to the first orientation of the system. A three dimensional image of the object is reconstructed using the measured geometric calibration data corresponding to the first orientation. An advantage that may be realized in the practice of some disclosed embodiments of the tomographic imaging system is improved radiographic image quality. In particular, improved accuracy and quality of reconstructed volume when existing calibration data does not exist or does not exactly match the imaging conditions. If an imaging system allows the production of geometrical calibration data post scan/exam acquisition, the application of this calibration data may remove image artifacts associated with non-matching geometric calibration data.

In one embodiment, a method of operating a tomographic imaging system is disclosed. A plurality of projection images of an object are captured using a first orientation of a source and a detector, then geometric calibration data is determined corresponding to the first orientation. A three dimensional image of the object is reconstructed using the projection images of an object and the determined geometric calibration data.

In another embodiment, a method of operating a tomographic imaging system is disclosed. A plurality of projection images of an object are captured at a first orientation of a source and a detector. A first 3-D volume image of the object is reconstructed using the projection images of the object and previously recorded geometric calibration data. The first reconstructed 3-D volume image may not satisfy a predetermined quality metric, therefore, a second set of geometric calibration data is obtained based on the first orientation. A second 3-D volume image of the object is reconstructed using the projection images of the object and the second set of geometric calibration data.

In another embodiment, a method of operating a tomographic imaging system is disclosed. A plurality of stored radiographic projection images of an object is accessed. An orientation of an imaging system that was used to capture the radiographic projection images is determined. Then, geometric calibration data for another imaging system is obtained according to the determined orientation of the imaging system used to capture the radiographic projection images. A 3-D image of the object is reconstructed using the radiographic projection images and the obtained geometric calibration data.

In another embodiment, a computer implemented method includes receiving radiographic projection images of an object captured by one imaging system and determining an orientation of the system used to capture the projection images. Geometric calibration data is received that corresponds to the determined geometry and orientation used by the imaging system to capture the projection images. The geometric calibration data is generated by another imaging system. A 3-D image of the object is reconstructed using the received projection images and the received geometric calibration data.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIGS. 2A-2C are perspective diagrams of an exemplary tomographic imaging system showing a portion of the internal components, a housing therefor, and a configuration for imaging an extremity of a patient;

FIGS. 3A-3C illustrate translations of the exemplary tomographic imaging system with respect to a γ axis, a z axis, and an α axis, respectively.

DETAILED DESCRIPTION OF THE INVENTION

Figure 1A:
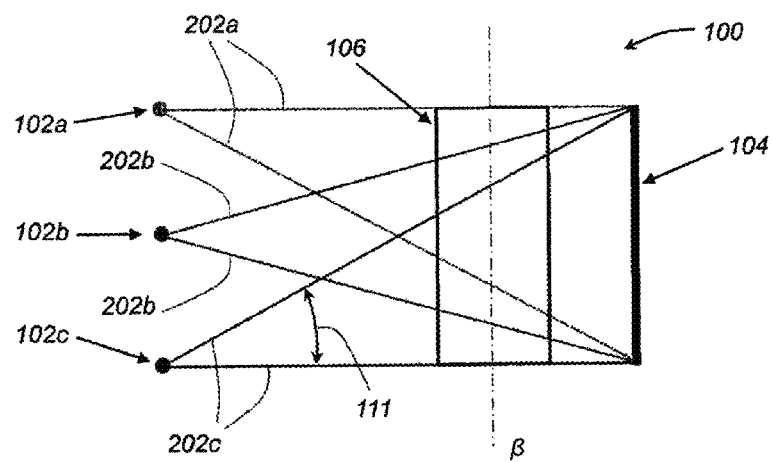
FIGS. 1A-1B are schematic diagrams of an exemplary multi-source tomographic imaging system.

With reference to FIG. 1A there is illustrated a schematic diagram of a tomographic imaging system 100 comprising one or more radiographic energy (x-ray) sources 102a-c aimed at an object 106 to be radiographically imaged. A digital radiographic (DR) detector 104 is positioned in a known and predetermined geometric spatial relationship with the x-ray sources 102a-c wherein the object 106 to be imaged is positioned therebetween. In one embodiment, the x-ray sources 102a-c and the DR detector 104 may form a portion of a CBCT imaging system 200 (FIGS. 2A-C), whereby one or more of the x-ray sources 102a-c and the detector 104 are configured to revolve about an imaging axis β while capturing a plurality of digital projection (2-D) images of the object 106 in the detector 104, as is well known in the digital radiography arts. The captured images may be processed in, or transmitted by, the detector 104. If transmitted, the detector 104 may use wired or wireless transmission means to transmit the captured images to an associated computer system for image processing, such as for reconstructing a 3-D image from a number of captured projection images.

Figure 1B:
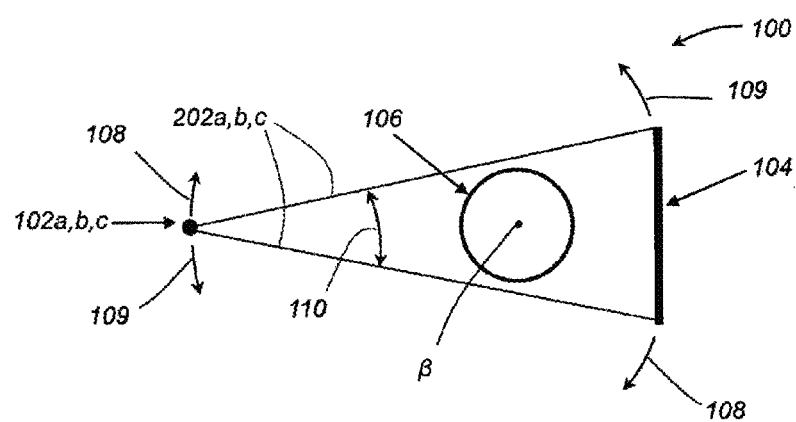

In one embodiment, the object to be imaged 106 is positioned so as to coincide with the imaging axis β, although such positioning is not required, and adequate images of the object 106 may be captured and reconstructed if the object 106 is positioned proximate to the imaging axis β. The one or more x-ray sources 102a-c may each be configured to controllably emit, or fire, an x-ray beam 202a-c, respectively, such as a cone beam, aimed at object 106 and toward the DR detector 104. The shapes of the x-ray beams 202a-c are not intended to illustrate a limiting shape of the x-ray beams 202a-c. Rather, they are intended to highlight the portion of the emitted x-ray beams that penetrate the object 106. FIG. 1B is a schematic top view of the imaging system 100 illustrating an embodiment of the imaging system 100 whereby the x-ray sources 102a-c are arranged collinearly in a line parallel to the imaging axis β.

In one embodiment, to complete a CBCT scan of the object 106, at least one of the sources 102a-c are selectively and controllably fired multiple times while simultaneously revolving both the selected one or more of sources 102a-c and the detector 104 about axis β for at least a portion of one revolution thereabout, i.e., 360° or less, in either of the directions indicated by arrows 108 or 109, while maintaining the selected one or more sources 102a-c and detector 104 diametrically opposed in relation to the axis β. Each firing of the selected one or more of the sources 102a-c generates a different radiographic projection image (2-D) of the object 106, depending on its angular position in relation to the imaging axis β, that is digitally captured by detector 104. In one embodiment, the selected one or more of the sources 102-a-c is fired multiple times at angular points equidistant from each other as it revolves about axis β during one complete revolution. In one embodiment, the selected one or more of the sources 102a-c is fired 360 times during one revolution (360° scan) about axis β, each firing occurring substantially one degree apart. In another embodiment, the selected one or more of the sources 102a-c is each fired 200 times during one revolution about axis β, each firing also occurring at angular points substantially equidistant from each other. In another embodiment, the selected one or more of the sources 102a-c is each fired 3600 times during one revolution about axis β, each firing also occurring at angular points substantially equidistant from each other.

In one embodiment, the selected one or more of the sources 102-a-c and the detector 104 revolve about the imaging axis β for less than a full 360 revolution, while capturing any number of projection images of the object 106. In one example, the selected one or more of the sources 102-a-c and the detector 104 revolve about the imaging axis β at an angle equivalent to 180° plus the cone beam angle 110. It will be recognized by persons skilled in the art that any number of images may be captured during one revolution of a selected one or more of the sources 102a-c and detector 104, limited only by the mechanical and electrical characteristics of the tomographic imaging system 100. To reconstruct a 3-D volume image of the object 106, each captured 2-D projection image is associated with geometric data that precisely defines the geometric position of the one or more fired sources 202a-c relative to the detector 104. As described herein, tomographic imaging systems allowing several degrees of freedom with respect to spatial positioning of the source and detector as well as spatial angles of the imaging axis β, may result in a large but finite number of possible relative spatial orientations as between the source and detector for each captured image.

It will be appreciated by one skilled in the art that x-rays are emitted from the one or more sources 102a-c with a representative predetermined cone beam angle 110 and a representative predetermined fan beam angle 111. During the digital image data acquisition procedure, which may be referred to herein as a scan, an imaging scan, a patient scan, a 360 scan, or a scanning sequence, for example, the one or more sources 102a-c travel over a predetermined curved trajectory, such as a circular trajectory embodiment, in relation to the object 106 in unison with the detector 104 such that the detector 104 acquires and transmits cone beam image data.

It is well known that imaging systems as depicted in FIGS. 1A-B are operable using only one of the x-ray sources 102a-c, and so may be configured with only one source 102 and one detector 104. Thus, the embodiments disclosed herein are not limited only to using multiple x-ray source 102a-c imaging systems 100 and are equally applicable to imaging systems using only one, or only two, of the x-ray sources 102a-c. Those having ordinary skill in the art will recognize that the system depicted in FIGS. 1A-B may be modified, as exemplified herein, without departing from the scope of the invention claimed herein.

Figure 2A:
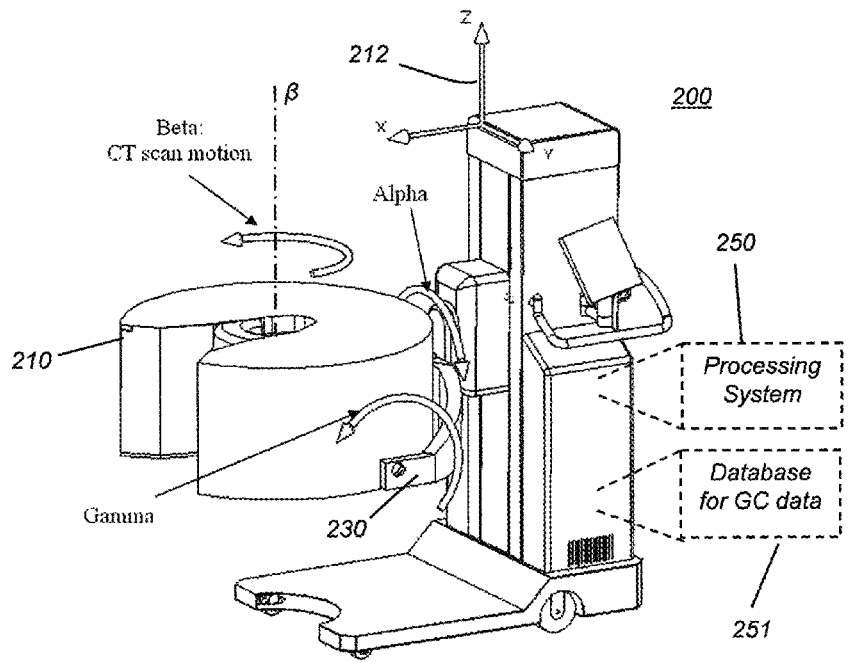
Figure 2B:
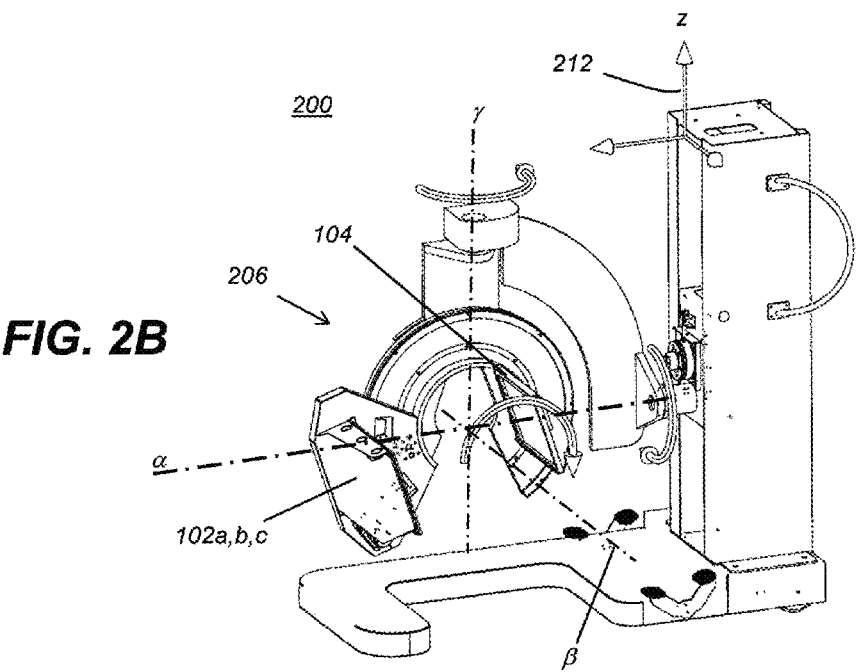

FIGS. 2A-2C illustrate portions of an exemplary mobile tomographic imaging system 200 that provides the imaging system 200 the capability for imaging patients in a variety of imaging configurations. FIGS. 2B-2C show rotation axes α, β, and γ, allowing variable positioning of the tomographic imaging system 200 similar in some respects to the positions described with respect to FIGS. 1A-B. As used herein the letters α, β, and γ will be used to refer to the variably adjustable axes and the corresponding terms alpha, beta, and gamma, respectively, will refer to the rotational directions. The fixed xyz coordinate system 212 may be used for reference. An α (alpha) axis and a γ (gamma) axis, as shown in FIG. 2B, allow gimbaled positioning of the source 102 and detector 104. The source 102 and detector 104 form part of a scanner assembly 206 that is enclosed within the scanner housing 210 as shown in FIGS. FIGS. 2A and 2C. According to one embodiment, the α-axis and the γ-axis are mutually orthogonal. In one embodiment, the α-axis is also substantially orthogonal to the z-axis. FIG. 2C illustrates an exemplary variable position of the tomographic imaging system 200 for scanning a lower extremity of a patient 250 positioned in the imaging bore of the system 200. The imaging bore may be defined as the space proximate the imaging axis β within a depth of the scanner housing 210.

With respect to the vertical z-axis, FIGS. 2A-C show exemplary embodiments configured to vertically position the source and detector using a vertical carriage to travel upwards and downwards along a support column parallel to the z-axis. A forked or C-shaped support arm 230 is attached to the scanner assembly 206 and allows rotation in the gamma direction, and is itself attached to a support column to allow rotation of the arm 230 and source and detector housing in the alpha direction. The x-ray source 102 and detector 104 are mounted on a curved or circular gantry to be revolved about the imaging axis β in the beta direction. Axis β is orthogonal to the α-axis and the γ-axis. Encoders, such as linear encoder elements, can be used to provide feedback signals indicating positions, or coordinates, of the scanner assembly components in each of the α, β, γ, and z axes which may be used to determine the position of the source and detector for each image captured during a scanning sequence. The position signals may be provided or interpreted as angular or distance measurements and such position data may be stored in association with each captured radiographic image.

It can be appreciated that z-axis translation may be effected in a number of ways as described in the related patent application entitled EXTREMITY IMAGING APPA- RATUS FOR CONE BEAM COMPUTED TOMOGRAPHY, and incorporated by reference herein. The tomographic imaging system 200 supports the weight of C-shaped support arm 230 as well as the scanning assembly 206 components including the source 102 and detector 104. These can easily weigh several hundred pounds and cause deflections in the source 102 and detector 104 scanning paths during an imaging scan revolution resulting in nonideal geometric variability. For example, as the source 102 and detector 104 revolve about the imaging axis β during an imaging scan, the actual orientation of the β axis may vary instantaneously during a revolution because of the mechanical load of the scanning assembly 206 due to earth gravity. Moreover, the instantaneous variation of the β axis during a scan will be different for each different α axis and γ axis orientation. Furthermore, the instantaneous variation of the β axis for the same α and γ orientations may change over time to material fatigue of the scanning assembly 206 components, adjustments due to repairs, mechanical wear and tear, etc. Thus, a total number of possible geometric calibration data sets corresponding to the total possible scanning orientations may be large and may change over time. In order to determine precise geometric calibration data for any spatial orientation of the tomographic imaging system 200, it may be necessary to perform a geometric calibration scan at a particular scanning orientation at the time of performing a patient exam using a known phantom to collect geometric calibration data. Use of phantoms to collect geometric calibration data is well known in the art.

In one example, geometric calibration data may be determined by placing a phantom having known geometrical features at a precise position in the imaging bore of the tomographic imaging system 200 and scanning the phantom by revolving the source 102 and detector 104 about the imaging axis β, as in a typical patient scan. In one embodiment, the imaging system 200 may be programmed to detect, transmit, and store encoder values corresponding to one or more of α, β, γ, and z axes coordinates corresponding to each captured image. As described herein the number of captured images may vary. In one embodiment, an encoder value may include a one dimensional value of an angle between 0 and 360 to represent alpha, beta, and gamma positions (for α, β, and γ axes), or a value representing a distance or height (for z axis). With each captured projection image, encoder values may be electronically stored in association with the captured image. The storage may be provided by processing system 250, database 251, or in a remotely accessible electronic storage. In one embodiment, coordinates representing at least alpha and gamma positions (angles) are stored with each captured image. In one embodiment, a default starting orientation of the scanning assembly 206 may be represented by the position of the imaging system 200 as illustrated in FIG. 2A. In one embodiment, the default starting orientation of FIG. 2A may be identified by default alpha and gamma values such as alpha=0° and gamma=0°. In one embodiment, increasing alpha angles may represent a clockwise rotation about the α axis as illustrated in FIG. 2A, while increasing gamma angles may represent a counter-clockwise rotation about the γ axis as illustrated in FIG. 2A. The measured and recorded geometric calibration data may be indexed or identified by its respective scanning orientation as identified by the alpha and gamma values used to capture the geometric calibration data.

A transformation matrix may be calculated using known 3-D coordinates of features of the phantom and transposing them onto the projected 2-D imaging plane of the detector 104. Thus, known 3-D locations of the phantom's features can be transposed onto the 2-D planar coordinates to generate the transformation matrix for each captured image. The transformation matrices may then be used to reconstruct a 3-D image of a patient anatomy whose projection images are captured at the same or similar orientations as the phantom. Solving for the unknown patient anatomy may be undertaken because the phantom geometry is known as well as the scanning assembly 206 geometry.

As described herein, a scanning orientation of the imaging system 200 may be identified or indexed by any one or more of alpha, beta, gamma, and z position coordinates, although the alpha and gamma coordinates alone may be used as an identifier. As described herein, the source and detector scan paths may not vary with respect to changes in z-axis position of the C-arm 230, although such variations may be expected with respect to changes in the alpha and gamma positions of the C-arm. The source and detector will revolve about the β axis with each scan, and so will vary in angular location with each fixed alpha and gamma orientation. As described herein, the one or more alpha, gamma, and z coordinates may be detected by encoders used to control a position of the C-arm of the imaging system 200. The obtained geometric calibration data may be stored and indexed, in database 251, according to an orientation identified by one or more of these orientation coordinates. For example, geometric calibration data may be stored in database 251 (FIG. 2A) for an α position of 0° and a γ position of 60°, which may correspond to the position of the imaging system 200 as depicted in FIG. 2C (i.e., the angle between the α axis and β axis is about 30°). A z-axis position value may also be used, however, in some embodiments it may not be necessary. The z-axis position may not be necessary if, for example, the z-axis of the imaging system coincides with a vector representing earth gravity at all z-axis positions of the scanning assembly, whereby deflections in the source and detector scan paths may not be expected to vary significantly with changes in z-axis height. However, it should be recognized that, depending on the structure of the imaging system 200, an increase in z-axis height of the scanning assembly may cause a corresponding increase in a bending moment imparted to the support column, thereby causing the z-axis to deviate from the earth gravity vector. Thus, it may be necessary to store and identify geometric calibration data using z-axis coordinate data in addition to the alpha and gamma coordinates. Similar considerations may be taken into account to determine whether it may be necessary to store and identify geometric calibration data using β axis coordinates in addition. For example, a patient scan may require a full 360° revolution, or a patient scan may require less than a full 360° revolution with variable starting and/or ending positions of the source and detector.

When the imaging system 200 is positioned to scan an extremity of a patient using orientation coordinates α=0°, γ=60° (FIG. 2C), for example, stored geometric calibration data may be accessed from database 251, according to those orientation coordinates, and a 3-D image reconstruction algorithm may be employed to generate a 3-D volume image of the patient extremity using the stored calibration data. Similarly, various scanning position coordinates may be used to search for comparable valid geometric calibration data. If acceptable calibration data is not available for a particular scanning orientation, the geometric calibration data may be generated after the patient scan is completed. The projection images generated by the patient scan may be stored, and a 3-D reconstruction algorithm may be later applied to the stored projection images after the geometric calibration data is generated. Thus, the geometric calibration data need not be available prior to performing a patient scan. In one embodiment, geometric calibration data may be available for orientation coordinates that are not exactly the same as a current patient exam but are within a predetermined allowable margin, for example, 5° or less. In such an embodiment, a control program algorithm may determine that the orientation coordinates are close enough to reconstruct a satisfactory 3-D volume image. In one embodiment, an operator of the imaging system 200 may evaluate the quality of a 3-D reconstructed patient anatomy image and determine that a better 3-D volume image can be obtained by generating new geometric calibration data at the exact orientation coordinates as used for the current patient anatomy image. Similarly, a quality metrics program may be used to automatically analyze a 3-D volume image to determine if image quality is unacceptable.

According to one embodiment, translation of the source 102 and detector 104 along the source and detector paths of the imaging system 200 may be manipulated by a motor controller using digitally encoded position coordinates. With respect to rotating the C-arm 230 about the α-axis, in one embodiment a rotational actuator can be energized to control rotation thereof. This rotational actuation may be concurrent with z-axis translation as well as with rotation of the scanning assembly 206 with respect to the γ-axis. As shown in the imaging system 200 orientation of FIG. 2B, the γ-axis is oriented vertically, substantially in parallel with the z-axis. FIG. 2A shows the γ-axis oriented horizontally. A rotational actuator provided in the control C-arm 230 allows rotation of the scanning assembly 206 about the γ-axis. As described herein, controlled movement of the C-arm 230 about the α-axis and the scanning assembly 206 about the γ-axis allows an almost unlimited number of spatial orientations of the scanning assembly 206. The gimbaled combination of α-axis and γ-axis rotation can allow the imaging apparatus 200 to be set up for imaging in a large number of possible positions, with a patient standing, seated, or prone. FIG. 2C shows the scanning assembly positioned for a foot or ankle exam with the patient 250 in a seated position. For this configuration, C-arm 230 is elevated above a minimum height with respect to the z-axis. Some slight adjustment about the α-axis may be useful for such an examination. Rotation about the γ-axis of about 60° from the default starting position (FIG. 2A) orients the scanner assembly 206 at a suitable angle for imaging.

An exemplary positioning capability of the tomographic imaging system 200 is shown in FIG. 3A-3C. FIG. 3A shows rotation of the scanning assembly about the γ-axis as illustrated by the position of the scanner housing 210. FIG. 3B illustrates movement of the scanning assembly along the support column to provide z-axis (vertical) translation of the scanning assembly. FIG. 3C shows rotation of C-arm 230 and scanner housing 210 about the α-axis.

In one embodiment, an operator input may initiate the tomographic imaging system 200 to automatically position the scanner assembly 206 in one of a well-defined set of default programmed starting orientations for patient imaging. These may be orientations for which exact geometric calibration data is stored in database 251 and is accessible by the imaging system 200. If any needed adjustments in height (z-axis) or rotation about the α or γ axes are made by the operator, the previously stored geometric calibration data may be unacceptable for use in a 3-D reconstruction algorithm due to possible image degradation caused thereby. Similarly, the previously stored geometric calibration data may be acceptable for use in the 3-D reconstruction due to acceptable deviation within a defined threshold. The operator may decide that a new geometric calibration scan may be performed to obtain geometric calibration data for the precise scanning orientation used in the patient scan. In addition to the z-axis translation and rotation about α and γ axes previously described, the mobile tomographic imaging system 200 may be rotated parallel to a floor to allow rotation of scanner 210 with respect to the z-axis as well as translation along the floor.

Figure 4:
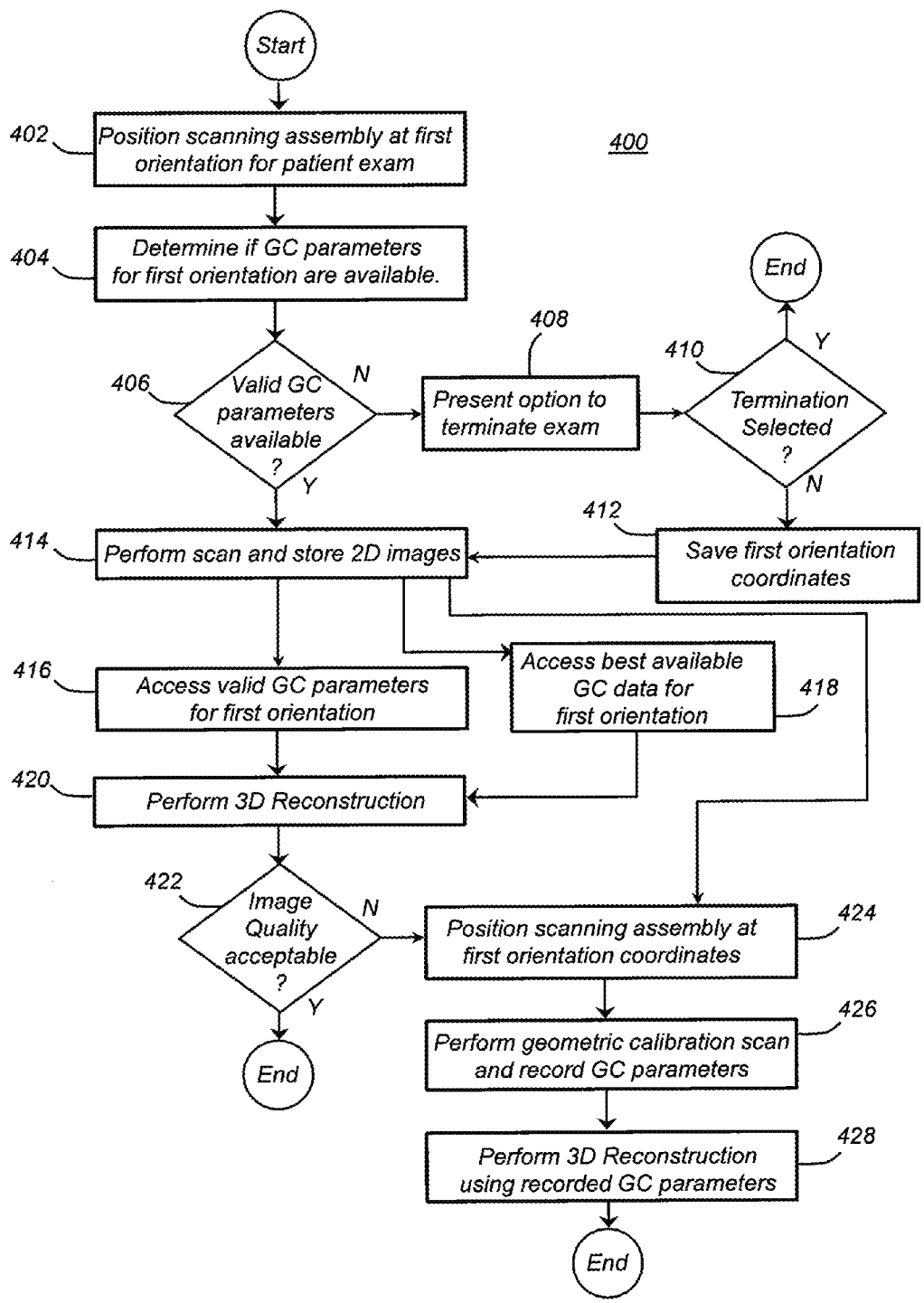
FIG. 4 is a flowchart illustrating an exemplary method of operating a tomographic imaging system.

FIG. 4 illustrates a flowchart of exemplary methods of operating a tomographic imaging system 200 as described herein. The flowchart may represent an algorithm performed entirely by program control stored in a processing system 250 incorporated within the imaging system 200 (FIG. 2A). At step 402, an operator of the tomographic imaging system 200 positions the scanning assembly 206 at a first orientation to perform a patient exam, which scanning assembly 206 may include a gantry, source 102, detector 104, as well as the scanner housing 210. The imaging system 200 may be programmed to automatically detect the first orientation of the scanning assembly 206 and to initiate an electronic search for stored geometric calibration (GC) data corresponding thereto, at step 404. Such a search may include searching a data base provided with the imaging system 200, or it may include searching a network connected database that is accessible by the imaging system 200, or accessible by a processing system that is used to control the imaging system 200, such as a workstation, laptop, or tablet computer connected to the imaging system 200. Thus, the search may be controlled by such a workstation, laptop, or tablet computer. In one embodiment, such a search may include searching a data base provided with another imaging system that may be similar in certain respects to the imaging system 200. Such other imaging system may be used in a same diagnostic facility as the imaging system 200, or it may be used at a distant diagnostic facility but accessible over a data communication network, such as the internet. Such other imaging system may be similar to the imaging system 200, such as embodying a same, a prior, or later, version of the imaging system 200. Such other imaging system may be dissimilar to the imaging system 200, except for having a similar geometry as the imaging system 200.

After completion of such a search, it may be determined that acceptable (valid) geometric calibration parameters (data) corresponding to the first orientation is not available, at step 406. Such a determination may include concluding that available geometric calibration data does not correspond to the first orientation within an acceptable threshold criterium, for example, either or both of the alpha and gamma positions of the available geometric calibration data are not within x degrees of the first orientation, such as within about five (5) degrees, for example. At step 408, the imaging system may present an option to the operator to terminate the patient exam due to the unavailability of the GC parameters. Such an option may be presented on a display associated with the imaging system 200 configured to receive operator inputs for controlling the imaging system 200. If the operator inputs an exam termination request in response, at step 410, the patient examination procedure ends. If, in response, the operator inputs a request to continue, at step 410, the coordinates that identify the first orientation are saved, at step 412, by the imaging system 200, which may include one or more of α, β, γ, and z axes coordinates. If it's determined that valid GC parameters are available after a search, at step 406, or if the operator chooses not to terminate the exam in the absence of valid GC parameters, at step, 410, the patient scan is performed and the 2-D projection images captured thereby are electronically stored at the imaging system 200 or in a data base that is accessible to the imaging system 200.

If valid GC parameters were determined to be available, at step 406, then the valid GC parameters are accessed, at step 416, and a 3-D image reconstruction using the captured 2-D projection images and the valid GC parameters is performed, at step 420. If valid GC parameters were determined not to be available, at step 406, then a set of best available GC parameters corresponding to the first orientation are accessed, at step 418, and a 3-D image reconstruction using the captured 2-D projection images and the best available GC parameters is performed, at step 420. Alternatively, the 3-D reconstruction using best available GC parameters may by bypassed, and the method may continue to generating new GC parameters, at step 424, after performing the patient scan at step 414.

After performing the 3-D image reconstruction, at step 420, using either the valid GC parameters or the best available GC parameters in relation to the first orientation, the image quality of the resulting 3-D reconstructed volume image may be evaluated, at step 422. Such evaluation may be automatically performed under program control by the imaging system 200 or by processing systems connected to the imaging system 200, as described herein. Such image analysis programs are known in the art. Alternatively, an operator of the imaging system 200 or another health care provider may subjectively determine whether the quality of the 3-D reconstructed image is acceptable. If the 3-D reconstructed image quality is determined to be acceptable, at step 422, the method is completed and ends. If the 3-D reconstructed image quality is determined to be unacceptable, at step 422, the method may continue to generating new GC parameters, beginning at step 424.

Generating new GC parameters (data) begins with positioning the scanning assembly 206 of the imaging system 200 at the first orientation, at step 424, using the orientation coordinates saved at step 412, and placing a known phantom in a known position within the imaging bore of the imaging system 200, as described herein. A geometric calibration scan of the phantom is performed, at step 426, to generate and record new GC parameters and, finally, a 3-D image reconstruction using the 2-D projection images of the patient captured at step 414 and the new GC parameters generated at step 426 is performed, at step 428, whereby the method is completed and terminates.

It should be noted that the methods depicted in the flowchart of FIG. 4 include alternative methods, as follows. In one embodiment, the method of FIG. 4 may include the steps of positioning the scanning assembly (step 402), followed by performing a scan of the patient and storing the 2-D projection images so obtained (step 414), followed by obtaining new GC parameters (steps 424 and 426), followed by performing the 3-D reconstruction (step 428) using the obtained 2-D projection images and the new GC parameters. In another embodiment, the method of FIG. 4 may include the steps of positioning the scanning assembly (step 402), followed by performing a scan of the patient and storing the 2-D projection images so obtained (step 414), followed by accessing the best available GC parameters (step 418), followed by performing the 3-D reconstruction (step 420) using the obtained 2-D projection images and the best available GC parameters. This may result in an unacceptable reconstructed 3-D image whereby obtaining new GC parameters is performed (steps 424 and 426), followed by performing the 3-D reconstruction (step 428) using the obtained 2-D projection images and the new GC parameters.

In one embodiment, as described herein, a second separate processing system, other than on-board processing system 250, may be communicatively coupled to the imaging system 200, locally or remotely, wirelessly or by physical direct connection, and may be used to control the imaging system 200. Such a processing system may include a workstation, server, laptop, or tablet computer, for example, connected to the imaging system 200. Relevant data may be transferred from the imaging system 200 to the processing system, such as geometric calibration data and associated 2-D projection images, whereby the connected processing system performs the 3-D volume image reconstruction using the transferred relevant data. The geometric calibration data and associated 2-D projection images may be generated close in time and location, such as during one day at one diagnostic facility, or they may be generated at different times separated by weeks or months, and at separate facilities nearby or across the world.

In one embodiment, as described herein, the imaging system 200 may be communicatively coupled to another imaging system that may be similar in certain respects to the imaging system 200. Such other imaging system may be used in a same diagnostic facility as the imaging system 200, or it may be used at a distant diagnostic facility but accessible over a data communication network, such as the internet. Such other imaging system may be similar to the imaging system 200 such as embodying a same, a prior, or later, manufacturing version, or generation, of the imaging system 200. Such other imaging system may be dissimilar to the imaging system 200, except for having a similar geometry as the imaging system 200. For example, a distance between the source and detector of the other imaging system may be similar or the same as that in the imaging system 200. Sizes of the respective detectors, path geometry traversed by the respective sources and detectors may be equivalent, and structure and/or weight distribution may be the same or equivalent as between the other imaging system and the imaging system 200. Hence, 2-D projection images of a patient anatomy captured by either of the imaging systems may be used to reconstruct a 3-D volume image of the patient anatomy using geometric calibration data generated by either of the imaging systems. In one embodiment, the reconstruction may be performed by a processor in either of the imaging systems or by a separate processing system connected to either of the imaging systems. Such a separate processing system may include a workstation, server, laptop, or tablet computer, for example, connected to the imaging system 200. Such a separate processing system may receive 2-D projection images of a patient anatomy captured by one of the imaging systems and transferred to the separate processing system, and receive geometric calibration data generated at the other imaging system and transferred to the separate processing system.

Other methods depicted in FIG. 4 may become apparent to those skilled in the art, and such methods may be included in the claims appended hereto, however, the methods recited in the claims appended hereto are not limited only to those depicted in FIG. 4.

As will be appreciated by one skilled in the art, aspects of the present invention may be embodied as a system, method, or computer program product. Accordingly, aspects of the present invention may take the form of an entirely hardware embodiment, an entirely software embodiment, including firmware, resident software, micro-code, etc., loaded in processing system 250, or an embodiment combining software and hardware aspects that may all generally be referred to herein as a "circuit," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may comprise a portion of processing system 250 and may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely in the on-board processing system 250, or on a separate computer, partly on the on-board processing system, as a stand-alone software package, partly on the on-board processing system and partly on a remote computer or entirely on the remote computer or server. In the latter scenario, the remote computer may be connected to the imaging system 200 or the processing system 250 through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of processing system 250, a separate special purpose computer, or other programmable data processing apparatus to produce a machine, such that the instructions, which execute via the processor of the computer or other programmable data processing apparatus, create means for implementing the functions/acts specified in the flowchart and/or block diagram block or blocks, via electronic communication with imaging system 200.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto processing system 250, other programmable data processing apparatus, or other devices to cause a series of operational steps to be performed by the imaging system 200.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of operating tomographic imaging systems that each include a source and a detector, the method comprising:
    capturing a plurality of first projection images of a first patient using the source and detector of a first imaging system at a first orientation of the source and detector;
    after the step of capturing, performing a calibration scan of a calibration object using the source and detector of the first imaging system to generate first geometric calibration data corresponding to the first orientation;
    capturing a plurality of second projection images of a second patient using the source and detector of a second imaging system at an orientation similar to the first orientation within a predetermined deviation; and
    reconstructing a three dimensional image of the second patient using the captured plurality of the second projection images and the generated first geometric calibration data corresponding to the first orientation.

2. The method of claim 1, further comprising determining the first orientation based on an angle of an imaging axis of the source and detector of the first imaging system.

3. The method of claim 2, wherein the step of performing a calibration scan comprises scanning a phantom using the source and detector of the first imaging system at the first orientation.

4. The method of claim 3, wherein the step of performing a calibration scan comprises measuring an amount of deflection of the source and detector of the first imaging system at the first orientation to generate the geometric calibration data.

5. The method of claim 1, further comprising determining that acceptable geometric calibration data is not available before the step of performing a calibration scan.

6. The method of claim 1, further comprising:
    transferring the plurality of second projection images to a processing system; and
    transferring the generated first geometric calibration data to the processing system,
    wherein the step of reconstructing is performed by the processing system.

7. A method of operating a tomographic imaging system that includes a source and a detector, the method comprising:

performing a calibration scan of a calibration object using the source and the detector of the tomographic imaging system to generate first geometric calibration data;

capturing a plurality of projection images of a patient at a first orientation of the source and the detector;

reconstructing a first 3-D volume image of the patient using the plurality of projection images of the patient and the first geometric calibration data;

determining that the first reconstructed 3-D volume image of the patient does not satisfy a predetermined quality metric;

after the step of determining, searching for and finding in a database second geometric calibration data that corresponds within a predetermined range to the first orientation of the source and the detector, wherein the second geometric calibration was generated by an imaging system different than the tomographic imaging system; and reconstructing a second 3-D volume image of the patient using the plurality of projection images of the patient and the found second geometric calibration data.

8. The method of claim 7, further comprising searching for and finding in the database third geometric calibration data generated by another imaging system different than the tomographic imaging system and reconstructing a third 3-D volume image of the patient using the plurality of projection images of the patient and the third geometric calibration data.

9. The method of claim 7, further comprising determining the first orientation based on at least two angular coordinates, wherein the at least two angular coordinates are based upon two separate and orthogonal axes.

10. The method of claim 9, further comprising scanning a phantom using the tomographic imaging system to generate the first geometric calibration data.

11. The method of claim 7, wherein the steps of reconstructing the first 3-D volume image and the step of reconstructing the second 3-D volume image are performed by a processing system accessible by the tomographic imaging system including transferring the plurality of projection images to the processing system and transferring the second geometric calibration data to the processing system.

12. A method of operating a first imaging system that includes a source and a detector, the method comprising:
  accessing a plurality of stored radiographic projection images of an object;
  determining an orientation of a second imaging system that was used to capture the plurality of stored radiographic projection images;
  after the steps of accessing and determining, obtaining geometric calibration data for the first imaging system based on the determined orientation of the second imaging system; and
  reconstructing a 3-D image of the object using the plurality of stored radiographic projection images and the obtained geometric calibration data.

13. The method of claim 12, further comprising determining that a geometry of the first imaging deviates from a geometry of the second imaging system within an acceptable margin.

14. The method of claim 12, further comprising determining the orientation of the second imaging system based on at least two angular coordinates, wherein the at least two angular coordinates are based upon two separate and orthogonal axes.

15. The method of claim 12, wherein the step of obtaining geometric calibration data for the first imaging system comprises scanning a phantom in the first imaging system after positioning the source and detector according to the determined orientation of the second imaging system.

16. The method of claim 12, further comprising accessing a 3-D image of the object that was reconstructed by the second imaging system including determining that the accessed 3-D image does not satisfy a selected quality criterion.

17. A computer implemented method comprising:
  receiving a plurality of radiographic projection images of an object captured by a first imaging system;
  determining an orientation of the first imaging system used to capture the plurality of radiographic projection images;
  receiving geometric calibration data corresponding to a geometry of the first imaging system and corresponding to the orientation used by the first imaging system to capture the plurality of radiographic projection images, wherein the geometric calibration data is generated by a second imaging system; and
  reconstructing a 3-D image of the object using the received plurality of radiographic projection images and the received geometric calibration data.

18. The method of claim 17, further comprising determining that a geometry and orientation used to generate the geometric calibration data by the second imaging system deviates within a predetermined margin from the geometry and orientation used by the first imaging system to capture the plurality of radiographic projection images, prior to the step of reconstructing.

19. The method of claim 17, further comprising searching over a network for, or sending a request over a network for, the received geometric calibration data.

* * * * *